(12) United States Patent
Wong et al.

(10) Patent No.: US 7,232,043 B2
(45) Date of Patent: Jun. 19, 2007

(54) USAGE INDICATOR

(75) Inventors: Kon Euan Wong, Glen Waverley (AU); John Ernest Oretti, Doncaster (AU)

(73) Assignee: Acrus DDS Pty Ltd (AU)

( * ) Notice: Subject to any disclaimer, the term of this patent is extended or adjusted under 35 U.S.C. 154(b) by 0 days.

(21) Appl. No.: 10/540,346

(22) PCT Filed: Dec. 22, 2003

(86) PCT No.: PCT/AU03/01714

§ 371 (c)(1), (2), (4) Date: Nov. 29, 2005

(87) PCT Pub. No.: WO2004/056416

PCT Pub. Date: Jul. 8, 2004

(65) Prior Publication Data
US 2006/0163276 A1   Jul. 27, 2006

(30) Foreign Application Priority Data
Dec. 20, 2002 (AU) .............................. 2002953483

(51) Int. Cl.
*B67D 5/22* (2006.01)

(52) U.S. Cl. .................................................. 222/38
(58) Field of Classification Search .................. 222/36, 222/38
See application file for complete search history.

(56) References Cited

U.S. PATENT DOCUMENTS

| | | | | |
|---|---|---|---|---|
| 2,966,175 | A | 12/1960 | Hyde et al. | |
| 4,565,302 | A * | 1/1986 | Pfeiffer et al. | 222/38 |
| 4,838,857 | A | 6/1989 | Strowe et al. | |
| 5,174,473 | A * | 12/1992 | Marelli | 222/38 |
| 5,209,375 | A * | 5/1993 | Fuchs | 222/38 |
| 5,289,946 | A * | 3/1994 | Fuchs | 222/38 |
| 5,421,482 | A | 6/1995 | Garby et al. | |
| 5,799,651 | A | 9/1998 | Garby et al. | |
| 6,142,339 | A | 11/2000 | Blacker et al. | |
| 6,213,984 | B1 | 4/2001 | Lane et al. | |
| 6,234,168 | B1 * | 5/2001 | Bruna | 222/36 |
| 6,485,471 | B1 | 11/2002 | Zivitz et al. | |

FOREIGN PATENT DOCUMENTS

| | | |
|---|---|---|
| GB | 2 054 381 A | 2/1981 |
| WO | WO-91/14467 A1 | 10/1991 |
| WO | WO-93/24167 A1 | 12/1993 |
| WO | WO-94/25090 A1 | 11/1994 |
| WO | WO-01/37909 A1 | 5/2001 |
| WO | WO-02/058767 A1 | 8/2002 |
| WO | WO-03/092773 A1 | 11/2003 |

* cited by examiner

*Primary Examiner*—Philippe Derakshani
(74) *Attorney, Agent, or Firm*—Lerner, David, Littenberg, Krumholz & Mentlik, LLP

(57) ABSTRACT

A substance dispensing device associated with a usage indicator is disclosed. The device includes a substance storage container and a pump operable to dispense substance from the container. The usage indicator includes a movable member that is movable in response to operation of the pump. The movable member includes an indicator providing a visual indication of the extent to which substance has been dispensed from the device.

12 Claims, 3 Drawing Sheets

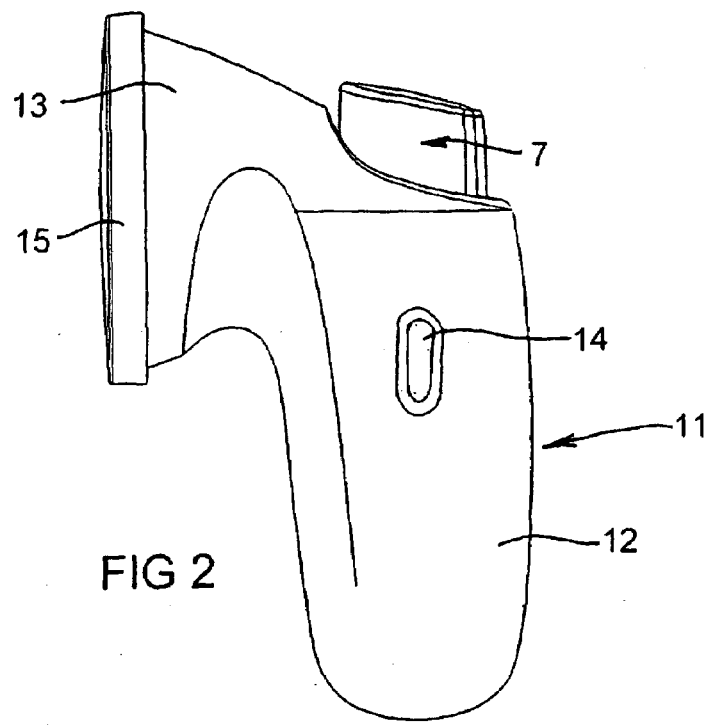
FIG 2
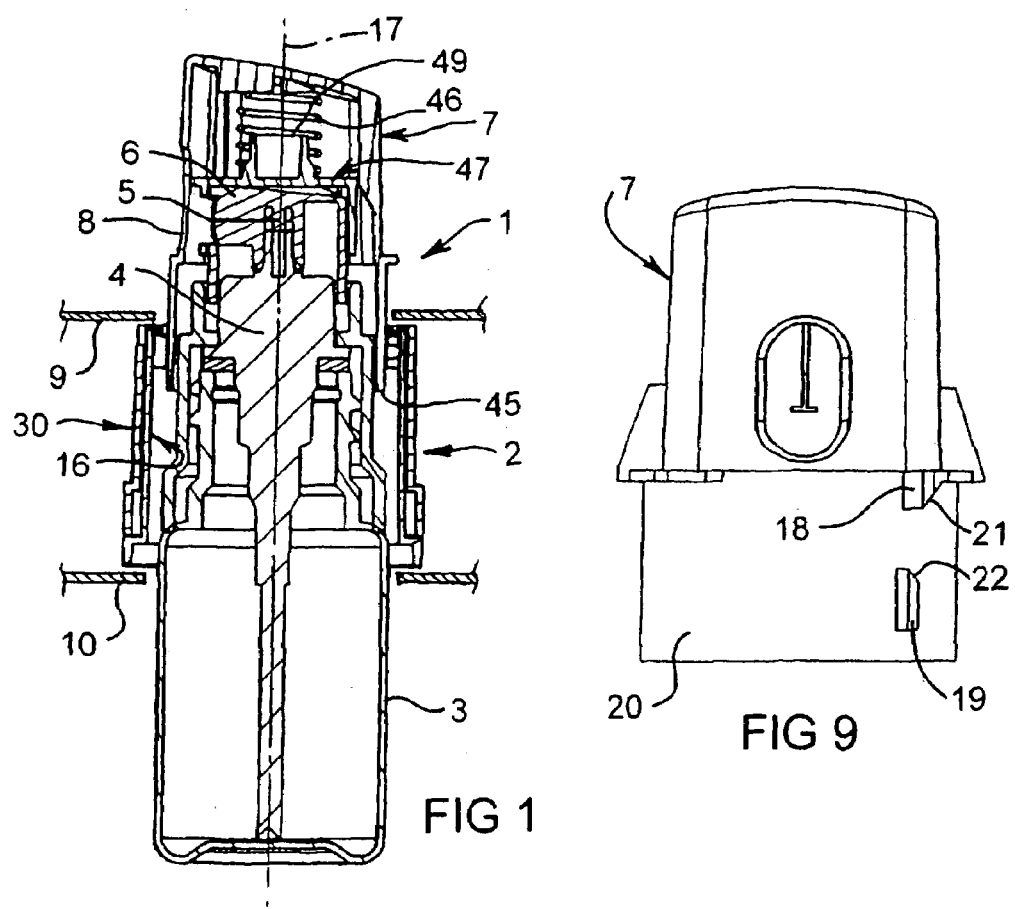
FIG 1
FIG 9

USAGE INDICATOR

FIELD OF THE INVENTION

This invention relates to means for indicating the extent to which a device has been used. The invention has particular, but not exclusive, application to devices for dispensing a substance, such as a pharmaceutical, medicinal, or therapeutic substance. It will be convenient to hereinafter describe the invention with reference to such dispensing devices intended for transdermal and/or percutaneous delivery of substances, but it is to be understood that the invention has broader application.

BACKGROUND OF THE INVENTION

It is usually the case that substance dispensing devices of the foregoing kind can be used on several occasions before the quantity of the substance stored in the device is exhausted. It is also a common requirement that an accurately metered amount of the substance is dispensed each time the device is operated.

Devices of the foregoing kind have been provided with means that enable the user to determine when the stored quantity of the substance is getting low. Various different arrangements have been provided for that purpose, but they have not been entirely satisfactory because of cost, lack of accuracy, or difficulty to read or interpret.

Another problem encountered with devices of the foregoing kind is the possibility of the device dispensing less than the intended quantity of the substance. That may occur because of inadequate care on the part of the operator, and may also occur because the stored quantity of the substance remaining in the device is too small at the time the device is operated.

It is an object of the present invention to provide a relatively inexpensive, accurate and easy to read usage indicator. It is a further object of the present invention to provide a substance dispensing device including such an indicator. Still another object of the invention is to provide a substance dispensing device having a usage indicator, and also having means preventing operation of the device when the quantity of the stored substance approaches exhaustion.

SUMMARY OF THE INVENTION

According to the present invention there is provided a substance storage container for containing substance to be dispensed; a pump, each operation of the pump dispensing a predetermined percentage of the substance stored in the container; and an actuator that is biased towards a rest position and is moved from the rest position to effect each operation of the pump and return to the rest position to enable subsequent operations of the pump; and a usage indicator having a movable member responsive to each operation of the pump, indicator means associated with the movable member providing a visual indication of the extent to which substance has been dispensed from the container. The movable member is moved in response to movement of the actuator away from its rest position. It is also preferred that the movable member is moved in response to movement of the actuator back to its rest position, so that two stage movement of the movable member represents a single operation of the pump.

It is preferred that the actuator is moved in the direction of an axis and the movable member is rotated about the axis, the actuator having drive means that cooperates with reaction means of the movable member to convert the axial movement of the actuator to rotational movement of the movable member about the axis. Preferably the drive means includes a pair of axially spaced lugs formed with the actuator and the reactive means includes two series of teeth formed with the movable member one series for each lug, the lugs being spaced axially so that only one lug can engage a tooth of its respective series of teeth at any one time.

It is preferred that the number of teeth in either series is selected according to the number of operations of the pump required to substantially exhaust the substance from its container. It is also preferred that the movable member is a first movable member and the usage indicator includes a second movable member, the second movable member cooperating with the first movable member to move only after the first movable member has completed one revolution, whereby complete revolution of both first and second movable members represents the number of operations of the pump required to substantially exhaust substance from the container. It is further preferred that the device include an interlock means cooperable with the usage indicator being activated after a predetermined number of operations of the pump to prevent further operation of the pump. Preferably the device includes a hollow body for accommodating the container, the pump and usage indicator, the body having an aperture through which the indicator means is viewed.

BRIEF DESCRIPTION OF THE DRAWINGS

It will be convenient to hereinafter describe the invention in greater detail by reference to the accompanying drawings showing an example embodiment of the invention. The particularity of the drawings and the related description of those drawings is not to be understood as superseding the generality of the definition of the invention as provided in the claims. The drawings show the usage indicator of the invention associated with a substance dispensing device.

FIG. 1 is a side, elevational, cross-sectional view of a substance dispensing device in accordance with the present invention;

FIG. 2 a side, elevational view of a housing for the dispensing device of the present invention;

FIG. 9 is a front, elevational view of the actuator button for use in the device of the present invention, including the lugs.

DETAILED DESCRIPTION

Figure 3:
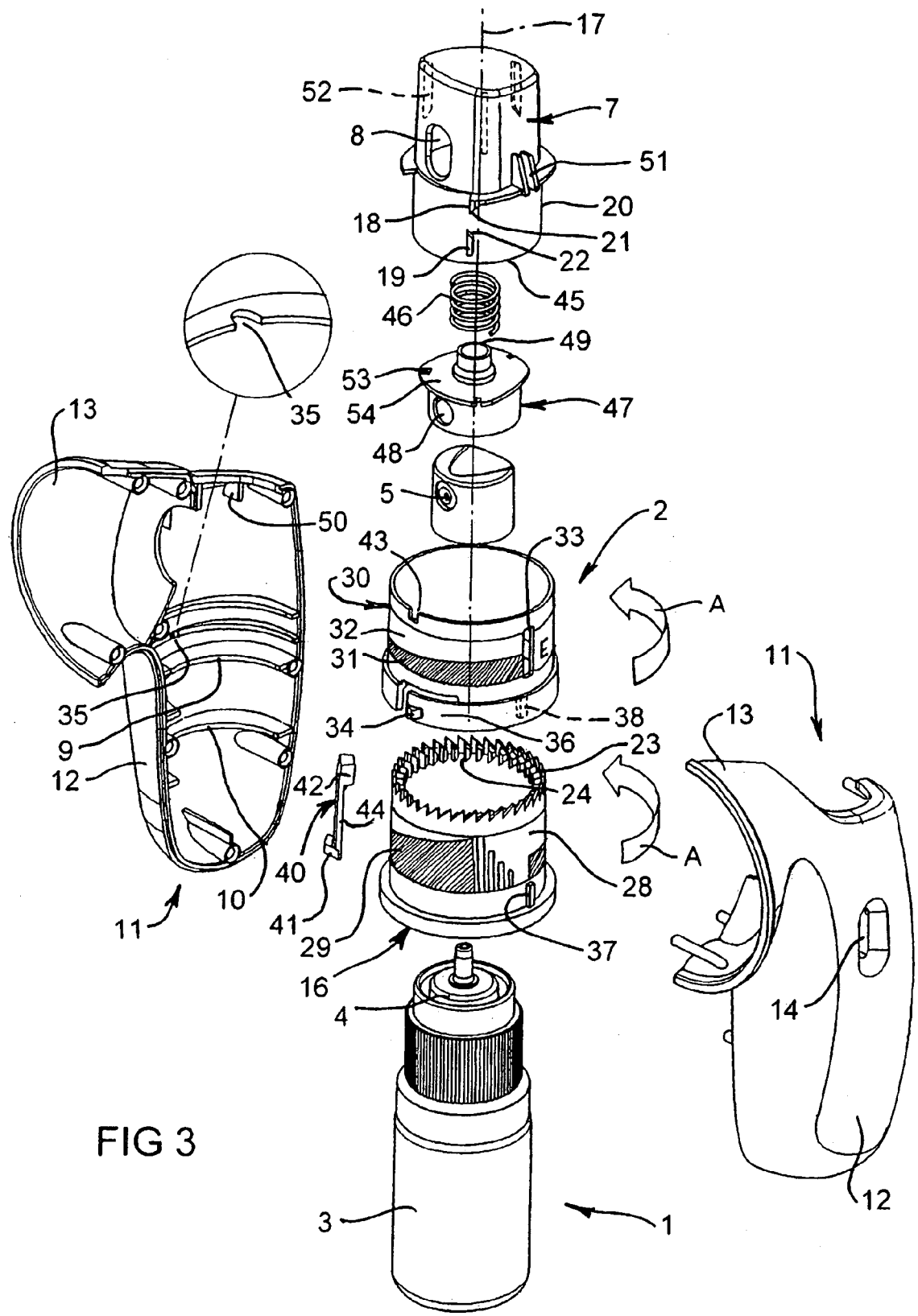
FIG. 3 is a side, perspective, exploded view of a substance dispensing device and housing of the present invention.

FIG. 1 shows an example substance dispensing device 1 associated with a usage indicator 2 according to one embodiment of the invention. The device 1 includes a substance storage container 3 and a pump 4 operable to pressurise the contents of the container 3 and thereby induce a quantity of the substance to be expelled through a nozzle 5, possibly in the form of a spray or mist. The pump 4 may be of a known kind that operates in a known manner in response to downward movement of the nozzle head 6 of the pump 4. In the particular arrangement shown, an actuator button 7 overlies the head 6 and cooperates with that head so that depression of the button 7 causes downward movement of the head 6. An opening 8 formed through a side wall of the button 7 is aligned with the nozzle 5 so as to allow passage of the substance expelled through the nozzle 5.

It is to be understood that the usage indicator 2 could be used with other types of dispensing devices, including aerosol-type dispensers.

In the arrangement shown by FIG. 1, the usage indicator 2 is located between two supports or retainers 9 and 10 that hold the indicator 2 against movement with the actuator button 7. The retainers 9 and 10 can be of any suitable form or construction. As hereinafter described in greater detail, the usage indicator 2 responds to operational movement of the actuator button 7 so as to indicate the extent to which the device 1 has been used.

FIG. 1 shows the button 7 in a rest position. Downward movement of the button 7 from that rest position causes operation of the pump 4, and it is preferred that biasing means functions to return the button 7 to the rest position when downward pressure is removed from the button 7. It is further preferred that the usage indicator 2 responds to downward movement of the button 7 away from the rest position, and also responds to return movement of the button 7 towards the rest position. That two-stage response is preferably representative of a single operation of the device 1.

FIG. 2 illustrates an example housing 11 for the dispensing device 1. The housing 11 includes a hollow body 12 for accommodating the container 3 and the pump 4, and a shroud 13 defining a space for receiving substance expelled through the nozzle 5. The usage indicator 2, or indicating means associated with the indicator 2, may be observable through an aperture or window 14 provided in a side wall of the body 12. A removable dust cap 15 may be located over the open mouth of the shroud 13 when the device 1 is not in use.

FIG. 3 is an exploded view of an assembly comprising the dispensing device 1, the device housing 11, and one particular form of usage indicator 2 according to the invention. In that assembly, the usage indicator 2 is supported or retained by location between two internal ledges 9 and 10 of the housing 11. A part of each ledge 9 and 10 may be provided in each of the two halves of the housing 11 shown by FIG. 3.

The particular usage indicator 2 shown in the accompanying drawings includes a member 16 that is mounted for rotation relative to the device housing 11. As shown, the member 16 is of cylindrical tubular form, but other forms could be adopted. Also, in the arrangement shown, the member 16 is rotatable about the longitudinal axis 17 of the device 1 (FIGS. 1 and 3), but that is not essential. Interactive means is provided to enable operational movement of the actuator button 7 to cause rotation of the member 16. Since the button 7 moves in the direction of the longitudinal axis 17 of the member 16, the interactive means includes means for converting linear movement of the button 7 into rotational movement of the member 16. For that purpose, the interactive means may include drive means connected to the button 7, and reactive means connected to the member 16 and positioned for engagement by the drive means during linear movement of the button 7. The drive means and the reactive means are preferably arranged so that during linear movement of the button 7, the drive means and the reaction means coact in a manner such that the member 16 is caused to rotate.

In the example shown, the drive means includes two drive lugs 18 and 19 that are connected to or formed integral with a lower skirt portion 20 of the actuator button 7. The drive lugs 18 and 19 are spaced apart in the direction of the axis 17 for a reason hereinafter made clear. A sloping face 21 is provided at the lower end of the uppermost lug 18, and a similar sloping face 22 is provided at the upper end of the lowermost lug 19. The sloping faces 21 and 22 are in opposed relationship, but as best seen in FIGS. 4 to 8 they slope in opposite directions—for example, at substantially 90° to one another. It is preferred, as shown by FIG. 9, that the face 21 extends outwards from the skirt portion 20 through a distance greater than the outward extension of the face 22.

One form of reactive means suitable for coaction with drive means of the foregoing kind includes two circular series of teeth, 23 and 24 respectively, connected to or formed integral with an upper edge portion of the member 16. In the arrangement shown, both series of teeth extend around the full circumference of the member 16, but that may not be the case in other embodiments of the invention. The teeth 23 and the teeth 24 are preferably of "saw-tooth" form as shown, but again that is not essential, and may not be adopted in other embodiments of the invention. As best seen in FIGS. 4 to 8, each tooth 23 has an upwardly facing sloping face 25 that is preferably substantially parallel to the face 21 of the lug 18, and each tooth 24 has a downwardly facing sloping face 26 that is preferably substantially parallel to the face 22 of the lug 19.

Figure 4:
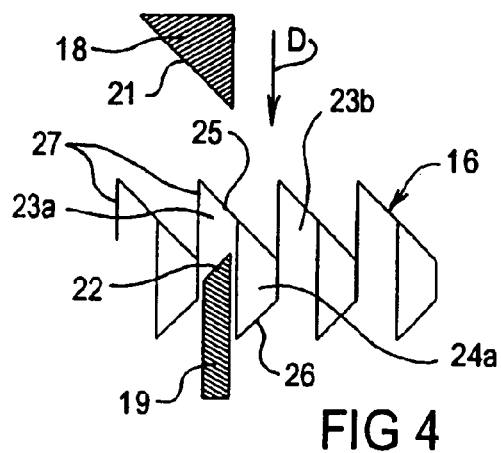
FIG. 4 is a side, elevational, schematic view of the manner in which the lug of an actuator button co-operate with teeth of a usage indicator in the operation of the device of the present invention.
Figure 6:
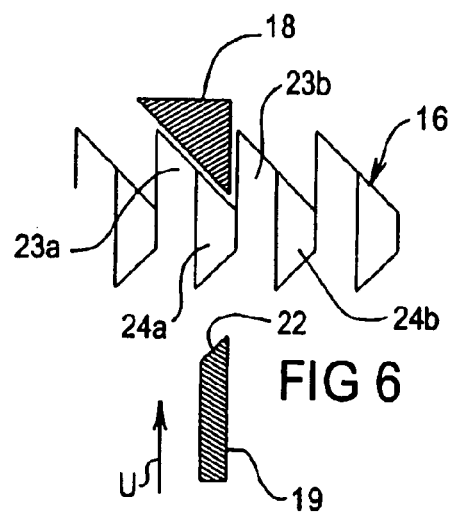
FIG. 6 is a side, elevational, schematic view of the manner in which the lug of an actuator button co-operate with teeth of a usage indicator in the operation of the device of the present invention.
Figure 7:
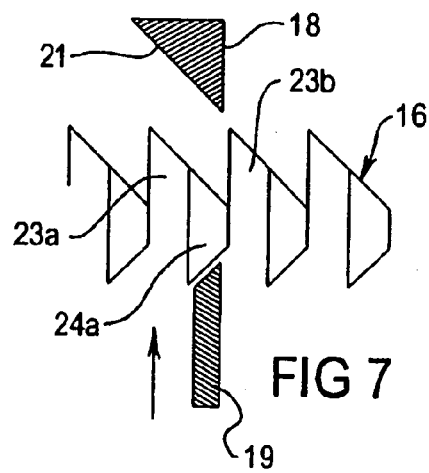
FIG. 7 is a side, elevational, schematic view of the manner in which the lug of an actuator button co-operate with teeth of a usage indicator in the operation of the device of the present invention.
Figure 8:
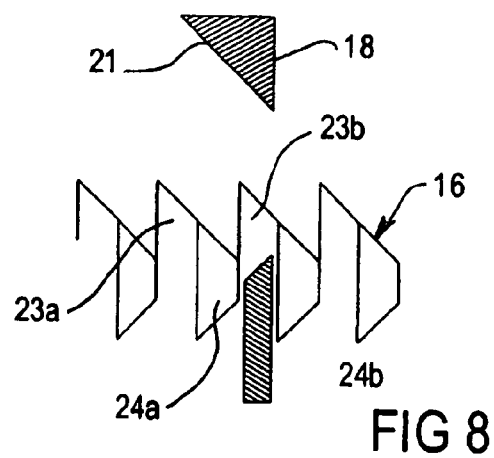
FIG. 8 is a side, elevational, schematic view of the manner in which the lug of an actuator button co-operate with teeth of a usage indicator in the operation of the device of the present invention.

FIGS. 4 to 8 provide a diagrammatic representation of the manner in which the lugs 18 and 19 cooperate with the teeth 23 and 24 respectively. Those Figures are representative of a cross-sectional view of the member 16, and consequently show the teeth 23 and 24 in the same disposition as that shown at the remote side of the member 16 as it appears in FIG. 3. It is particularly important to note that the interaction between the lugs 18 and 19 and the teeth 23 and 24 as shown by FIGS. 4 and 8, causes the member 16 to rotate in the anti-clockwise direction as indicated by the arrows A in FIG. 3. Subsequent reference in this specification to the "leading side" or "trailing side" of a part of the assembly is to be understood as referring to travel in the direction of arrows A.

Figure 5:
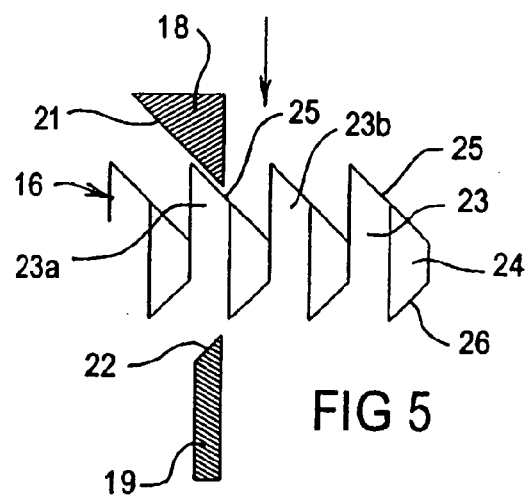
FIG. 5 is a side, elevational, schematic view of the manner in which the lug of an actuator button co-operate with teeth of a usage indicator in the operation of the device of the present invention.

When the usage indicator 2 is installed on the device 1, the two series of teeth 23 and 24 are both located between the drive lugs 18 and 19, as shown by FIGS. 4 to 8. Downward movement of the button 7 in the direction of arrow D (FIG. 4) brings the face 21 of the lug 18 into engagement with the face 25 of a tooth 23a (FIG. 5). Continued downward movement of the button 7 produces a coaction between the faces 21 and 25 such that the member 16 is caused to rotate to the left as shown by FIG. 6. At that stage, the button 7 has been depressed to its full extent and the pump 4 has been operated as required. Release of pressure on the button 7 then allows associated biasing means to move the button 7 upwards in the direction of arrow U (FIG. 6) towards the rest position. The face 22 of the lug 19 is thereby brought into engagement with the face 26 of a tooth 24a (FIG. 7). Continued upward movement of the button 7 then causes the member 16 to be rotated further to the left (FIG. 8).

When the member 16 is at the position shown by FIG. 6, it has been shifted to the left (from the FIG. 5 position) by approximately one half of an increment of the movement intended for the member 16 in response to each operation of the pump 4. When the member 16 is at the position shown by FIG. 8, it has moved to the left (from the FIG. 5 position) through a complete increment of movement. The tooth 23a which is engaged by the lug 18 in the FIG. 5 position, is now located to the left out of the path of the lug 18. Another tooth, 23b, is now located in the path of the lug 18 and will be engaged by that lug when the device 1 is next operated.

The increment of movement of the member 16 that occurs with each operation of the device 1, is through a distance substantially equal to the length of a tooth 23. That is, it is substantially equal to the distance between the upright faces 27 of two adjacent teeth 23 (FIG. 4).

The number of teeth in each series of teeth 23 and 24 will be selected according to requirements. One factor of possible influence is the number of operations of the pump 4 required to completely exhaust, or substantially exhaust, the stored contents of the container 3.

Part of the outer surface 28 of the member 16 may be observable through the window 14. Any suitable indicator means may be provided on the surface 28 (FIG. 3) to indicate, at the window 14, the extent to which the device 1 has been operated. By way of example, the indicator means may be a series of numbers, a respective one of which becomes observable at the window 14 after each operation of the device 1. In the particular example shown by FIG. 3, the indicator means is a band 29, possibly of a distinctive colour, that progressively changes in width around the circumference of the member 16. Only a small segment of the band 29 is observable at the window 14 at any one point in time. A maximum width segment of the band 29 may be visible at the window 14 when the device 1 is to be operated for the first time, and a minimum or zero width segment may be visible when there is little or no substance remaining in the container 3.

In some circumstances the number of possible operations of the pump 4 may exceed the number of teeth 23 capable of being provided on the member 16. That is, the member 16 must be moved through more than one complete revolution in order to exhaust, or substantially exhaust, the contents of the container 3. One solution to that problem is to provide the usage indicator 2 with a second movable member 30 (FIG. 3) that provides an indication of the extent of use of the device 1 during part of the time the pump 4 is capable of effective operation. In that regard, "effective operation" is to be understood as operation capable of delivering a substantially complete dose, or metered quantity, of the stored substance through the nozzle 5.

FIG. 3 illustrates an example arrangement involving use of a second movable member 30. In that particular arrangement, both members 16 and 30 are of cylindrical tubular form, and the second member 30 is located over the member 16. It will be convenient to hereinafter refer to the members 16 and 30 as the inner and outer members respectively. Indicator means 31 is provided on the outer surface 32 of the outer member 30, and it is preferred (as shown) that the indicator means 31 is of a style consistent with the style of the indicator band 29 of the inner member 16. It is particularly preferred that each of the two indicator bands 29 and 31 form a respective part of a continuous sequence of use indications. As previously stated, indicator means other than a band-type indicator means may be employed.

In the example arrangement of FIG. 3, the two members 16 and 30 are arranged so that the outer member remains stationary while the inner member 16 is rotated through a first series of increments of movement. That first series may be equal to, or substantially equal to, a complete revolution of the inner member 16. At the end of that first series of movements however, the two members 16 and 30 become connected in a manner such that further rotation of the inner member 16 causes corresponding rotation of the outer member 30. It is preferred that the indicator band 29 of the inner member 16 is observable at the window 14 during the first series of increments of movement, and that the indicator band 31 of the outer member 30 becomes observable at the window 14 after that first series has been completed. For that purpose, an opening 33 may be provided through a wall of the outer member 30 so as to be aligned with the window 14 when the member 30 is at an initial inactive position relative to the device body 12. The indicator band 29 of the inner member 16 is therefore observable through the window 14 and the aligned opening 33.

Releasable stop means, of any appropriate form, may be employed to hold the outer member 30 against rotation with the inner member 16 during the first series of increments of movement. In the particular example shown by FIG. 3, such stop means includes a detent 34 provided on the outer member 30, and a cooperable recess 35 provided on an inner surface of the housing body 12. The detent 34 may be connected to the main body of the outer member 30 through a flexible arm 36 so as to permit the detent 34 to be disengaged from the recess 35 in circumstances hereinafter described. Other means may be adopted for that purpose.

Any suitable connecting means may be employed to connect the members 16 and 30 for simultaneous rotation after completion of the first series of incremental movements of the member 30. In the particular example shown by FIG. 3, the connecting means includes at least one drive abutment 37 provided on the outer surface 28 of the inner member 16, and at least one cooperable abutment 38 provided on an inner surface of the outer member 30. Before initial operation of the device 1, the drive abutment 37 may be located against, or close to, the right-hand or leading side of the cooperable abutment 38. Each time the device 1 is operated, the drive abutment 37 will be moved (in an anti-clockwise direction as shown by the arrows A in FIG. 3) further away from the right-hand side of the cooperable abutment 38. When the inner member 16 approaches completion of a full revolution, the drive abutment 37 engages the left-hand or trailing side of the cooperable abutment 38, and at that time the two members 16 and 30 become connected for simultaneous rotation.

When the device 1 is operated immediately following engagement of the abutments 37 and 38, the inner member 16 imposes a turning force on the outer member 30 that is sufficient to cause the detent 34 to be released from engagement with the recess 35. For that purpose, the detent 34 and/or the recess 35 may be provided with at least one sloping side surface that produces a camming action when pressed against an opposing surface of the recess 35 and/or the detent 34. The camming action is such as to induce the detent 34 to move out of the recess 35, and that movement is made possible by the flexibility of the arm 36.

The outer member 30 is thereby freed to rotate with the inner member 16. At the commencement of that simultaneous rotation the opening 33 is moved out of alignment with the window 14, and a segment of the indication band 31 of the outer member 30 becomes observable at the window 14. The indication band 29 of the inner member 16 is no longer observable because of the shift in the position of the opening 33.

It is preferred that the device 1 is provided with interlock means that is operative to prevent operation of the device 1 when there is little or no substance remaining in the container 3. In the preferred arrangement hereinafter described, the interlock means is responsive to the usage indicator so as to be rendered operative when the device 1 has been operated a predetermined number of times. It will be appreciated that other arrangements could be adopted.

The example interlock shown by FIG. 3 includes a locking bar 40 that extends generally in the direction of the axis 17 and is located within the housing body 12 between the inner surface of that body and the outer member 30 of the usage indicator 2. A lower end 41 of the bar 40 may be secured to an inside surface of the housing body 12 in any appropriate manner. A head portion 42 at the upper end of the bar 40 is engageable within an interlock recess 43 of the outer member 30 in appropriate circumstances as hereinafter described. An intermediate portion 44 of the bar 40 is sufficiently flexible to allow the head portion 42 to move between inoperative and operative positions as hereinafter described.

When the device 1 is conditioned for initial operation, the interlock head portion 42 is positioned to one side of the recess 43, and is therefore at an inoperative position. In the particular arrangement shown by FIG. 3, the head portion 42 is initially located relative to the recess 43 so that clockwise movement of the outer member 30 in the direction of arrows A (FIG. 3) progressively moves the recess 43 into alignment with the head portion 42. The initial relative positioning of the head portion 42 and the recess 43 will be selected according to the extent to which the outer member 30 is intended to be rotated before the interlock becomes operative. During that rotation of the outer member 30, the intermediate portion 44 of the bar 40 remains in a resiliently distorted state such that the head portion 42 is pressed against the outer surface 32 of the outer member 30.

At completion of the intended rotational movement of the outer member 30, the recess 43 is aligned with the head portion 42, thereby allowing the head portion 42 to snap engage within the recess 43 and thereby adopt an operative position. Further rotation of the outer member 30 is prevented by that engagement, and further rotation of the inner member 16 is also prevented because of engagement between the abutments 37 and 38. Such prevention of rotation of the member 16 and 30 may be sufficient to prevent further operation of the device 1. It is preferred however, that the interlock bar 40 also functions to prevent further operation of the device 1. For that purpose, the bar 40 is arranged to prevent the actuator button 7 being moved downward from the rest position to an extent such that coaction can occur between the lug 18 and a tooth 23 of the usage indicator 2. As will be apparent from the foregoing description, such coaction is necessary in order for the device 1 to operate.

Such locking of the actuator button 7 may be effected in any suitable manner. In the particular arrangement shown however, when the head portion 42 is within the recess 43, it is positioned directly beneath the lower edge 45 of the button 7. Downward pressure on the button 7 therefore results in the lower edge 45 engaging the head portion 42, and further downward movement of the button 7 is prevented.

It may be desirable to limit operation of the pump 4 to part only of the available downward travel of the button 7. In such circumstances a suitable lost motion facility may be incorporated in the device 1, or associated with the device 1. One such lost motion facility is shown in the example arrangement of FIG. 3. In that arrangement the button 7 is normally held elevated from the nozzle head 6 by a coil compression spring 46. The spring 46 may form at least part of the biasing means that functions to return the button 7 to the rest position after each operation of the device 1. Another part of that biasing means may be formed by a return spring (not shown) for the pump 4. It is preferred as shown, that the spring 46 acts between the button 7 and a cap 47 positioned over the nozzle head 6. The cap 47 has an opening 48 that is aligned with both the nozzle 5 and the button opening 8 so as to allow passage of substance expelled through the nozzle 5.

The arrangement is preferably such that operation of the pump 4 does not commence until the button 7 engages against an upper end 49 of the cap 47 and thereafter presses the cap 47 downwards. The nozzle head 6 moves downwards with the cap 47 and thereby causes operation of the pump 4 in a known manner. It is preferred that the lug 18 does not engage with a tooth 23 of the usage indicator 2 until operation of the pump 4 commences, or is about to commence.

Retaining means may be provided to prevent rotational movement of the button 7 out of the position at which the opening 8 is aligned with the nozzle 5. The same means, or different means, may be adopted to prevent rotational movement of the cap 47 out of the position at which the opening 48 is aligned with the nozzle 5.

In the FIG. 3 arrangement, the retaining means includes guide means acting between the button 7 and the housing body 12. In the example shown, that guide means includes a guide rib 50 provided on an inner surface of the body 12, and a cooperative guide groove 51 provided on the outside surface of the button 7. Both the rib 50 and the groove 51 extend generally in the direction of the axis 17, and the guide rib 50 is slidably located within the groove 51.

Similar guide means may be provided between the button 7 and the cap 47. In the arrangement shown by FIG. 3, at least one guide rib 52 is provided on an inside surface of the button 7 and is slidably located in a cooperative recess 53 provided in a laterally extending flange 54 of the cap 47. That arrangement prevents relative rotation of the button 7 and the cap 47, but permits the button 7 to be moved downwards relative to the cap 47. Other arrangements could be adopted to achieve the same result. Relative rotation between the cap 47 and the nozzle head 6 may be prevented, or resisted, by forming the cap 47 so that it is a press fit on the nozzle head 6.

Any suitable means may be adopted to ensure, or encourage, proper location of the device 1 within the housing 11 such that the nozzle 5 is aligned with the shroud 13.

It will apparent from the foregoing description that the present invention provides a relatively simple, accurate, and easy to read usage indicator for devices intended to be operated or used on a number of occasions. The inclusion of an interlock that is responsive to the usage indicator can be of significant benefit in at least some circumstances.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A substance dispensing device configured to indicate the extent to which said substance has been dispensed therefrom, said device having an axis along the longitudinal length of the device, said device comprising:
    a substance storage container for containing said substance to be dispensed;
    a pump, whereby each operation of said pump will dispense a predetermined percentage of said substance stored in said substance storage container;
    an actuator biased towards a rest position and movable from said rest position to effect each operation of said pump and return to said rest position to enable subsequent operations of said pump, said actuator including drive means including a pair of axial drive lugs spaced apart in the direction of said axis, each of said pair of drive lugs including a sloping face; and
    a usage indicator including a movable member rotatable about said axis in response to each operation of said pump, and indicator means associated with said movable member providing a visual indication of the extent to which said substance has been dispensed from said substance storage container, said movable member including reactive means comprising a pair of series of circumferentially arranged teeth, said teeth in each of said pair of series of circumferentially arranged teeth including a sloping face configured to sequentially cooperate with the sloping face of each of said pair of drive lugs to convert said axial movement of said actuator to rotational movement of said movable member about said axis, said sloping faces of each series of teeth being spaced apart in the direction of the axis,
    whereby when said actuator is moved in the direction of said axis away from said rest position to effect each operation of said pump one of said pair of drive lugs cooperates with one of said teeth in one of said pair of series of circumferentially arranged teeth to rotate such movable member about said axis and when said actuator returns to said rest position the other of said pair of drive lugs cooperates with one of said teeth in the other of said pair of series of circumferentially arranged teeth to further rotate said movable member about said axis.

2. A substance dispensing device according to claim 1, wherein each time said movable member is moved in response to movement of said actuator away from and back to said rest position, a single operation of said pump is represented on said usage indicator.

3. A substance dispensing device according to claim 1, wherein the number of said teeth in said pair of circumferentially arranged teeth is selected based upon the number of operations of said pump required to substantially exhaust said substance from said substance storage container.

4. A substance dispensing device according to claim 3, wherein said movable member comprises a first movable member, and said usage indicator includes a second movable member, said second movable member cooperating with said first movable member to move only after said first movable member has completed one revolution, whereby complete revolution of both said first and second movable members represents the number of operations of said pump required to substantially exhaust said substance from said substance storage container.

5. A substance dispensing device according to claim 1, including interlock means cooperable with said usage indicator, whereby said interlock means is activated after a predetermined number of operations of said pump to prevent further operation of said pump.

6. A substance dispensing device according to claim 1 including a hollow body for accommodating said substance storage container, said pump and said usage indicator, said hollow body having an aperture through which said indicator means is viewed.

7. A substance dispensing device according to claim 1, wherein said pair of drive lugs are axially spaced so that one of said pair of drive lugs can engage one of said pair of series of circumferentially arranged teeth at any one time.

8. A substance dispensing device according to claim 1, wherein said pair of series of circumferentially arranged teeth include a first series of teeth having an upwardly facing sloping face relative to said axis and a second series of teeth having a downwardly facing sloping face relative to said axis and wherein said pair of drive lugs include a first drive lug having a downwardly facing sloping face relative to said axis which cooperates with said upwardly facing sloping face of said first series of teeth and a second drive lug having an upwardly facing sloping face relative to said axis which cooperates with said downwardly facing sloping face of said second series of teeth.

9. A substance dispensing device according to claim 4, wherein said first and second movable members are concentrically arranged, with said second movable member being seated within said first movable member.

10. A substance dispensing device according to claim 9, including a releasable stop to hold said second movable member with said first movable member during said first revolution, said releasable stop comprising a detent located in one of said first and second movable members and a cooperable recess located in the other of said first and second movable members.

11. A substance dispensing device according to claim 10, wherein said detent is connected to said first or second movable members through a flexible arm.

12. A substance dispensing device according to claim 9, wherein said indicator means comprises first indicator means associated with said first movable member and a second indicator means associated with said second movable member providing a visual indication associated with said first indicator means to form a continuous sequence of use indications of the extent to which said substance has been dispensed from said substance storage container.

* * * * *

UNITED STATES PATENT AND TRADEMARK OFFICE
CERTIFICATE OF CORRECTION

PATENT NO. : 7,232,043 B2  Page 1 of 1
APPLICATION NO. : 10/540346
DATED : June 19, 2007
INVENTOR(S) : Kon Euan Wong and John Ernest Oretti It is certified that error appears in the above-identified patent and that said Letters Patent is hereby corrected as shown below:

On the Title Page, Item (73) Assignee: delete "Acrus" and insert therefor --Acrux--.

Signed and Sealed this

Eleventh Day of September, 2007

JON W. DUDAS
*Director of the United States Patent and Trademark Office*